(12) United States Patent
Seebeck et al.

(10) Patent No.: US 10,619,199 B2
(45) Date of Patent: Apr. 14, 2020

(54) NUCLEIC ACID AMPLIFICATION AND LIBRARY PREPARATION

(71) Applicant: SIGMA-ALDRICH CO. LLC, St Louis, MO (US)

(72) Inventors: Timothy Seebeck, St Louis, MO (US); Fuqiang Chen, St Louis, MO (US); Brian W Ward, St Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 198 days.

(21) Appl. No.: 15/550,563

(22) PCT Filed: Mar. 4, 2016

(86) PCT No.: PCT/US2016/021023
§ 371 (c)(1),
(2) Date: Aug. 11, 2017

(87) PCT Pub. No.: WO2016/144810
PCT Pub. Date: Sep. 15, 2016

(65) Prior Publication Data
US 2018/0037946 A1 Feb. 8, 2018

Related U.S. Application Data

(60) Provisional application No. 62/129,525, filed on Mar. 6, 2015.

(51) Int. Cl.
C12Q 1/68 (2018.01)
C12Q 1/6853 (2018.01)
C12N 15/09 (2006.01)
C12P 19/34 (2006.01)

(52) U.S. Cl.
CPC ........... *C12Q 1/6853* (2013.01); *C12N 15/09* (2013.01); *C12P 19/34* (2013.01); *C12Q 2521/319* (2013.01); *C12Q 2525/125* (2013.01); *C12Q 2527/143* (2013.01)

(58) Field of Classification Search
CPC .................................................. C12Q 1/6853
USPC ........................................................ 435/6.12
See application file for complete search history.

(56) References Cited

U.S. PATENT DOCUMENTS

| | | |
|---|---|---|
| 2011/0287510 A1 | 11/2011 | Nelson, Jr. |
| 2012/0295819 A1* | 11/2012 | Leamon ............... C12Q 1/6806 506/26 |
| 2014/0287468 A1 | 9/2014 | Richard |

FOREIGN PATENT DOCUMENTS

WO 2014018093 A1 1/2014

OTHER PUBLICATIONS

Howland et al. "Directional, seamless, and restriction enzyme-free construction of random-primed complementary DNA libraries using phosphorothioate-modified primers" Analytical Biochemistry 416 (2011) 141-143 (Year: 2011).*

(Continued)

*Primary Examiner* — Jezia Riley
(74) *Attorney, Agent, or Firm* — Sigma-Aldrich Co. LLC (57) ABSTRACT

Processes and kits for preparing a plurality of amplification products with reduced non-specific amplification artifacts.

16 Claims, 7 Drawing Sheets

Specification includes a Sequence Listing.

(56) References Cited

OTHER PUBLICATIONS

Nikiforov, TT et al. The Use of Phosphorothioate Primers and Exonuclease Hydrolysis for the Preparation of Single-stranded PCR Products and their Detection by Solid-Phase Hybridization. PCR Methods Appl. 3(5) 1994, 285-291.
International Search Report for PCT/US2016/21023 dated May 23, 2016 (4 pages).

* cited by examiner

NUCLEIC ACID AMPLIFICATION AND LIBRARY PREPARATION

FIELD OF THE INVENTION

The present disclosure relates to nucleic acid amplification and, in particular, to processes for preparing a plurality of amplification products with reduced non-specific amplification artifacts.

BACKGROUND

Targeted genome sequencing by the next generation sequencing (NGS) technology has become a powerful platform for biomedical and agricultural genome analyses, such as human identity and ancestry identification, disease diagnostics, plant germplasm molecular characterization, and molecular breeding. While the capacity of NGS platforms advances rapidly, the preparation of NGS-ready DNA libraries has become a limiting factor. Multiplex PCR is an ideal platform for high throughput production of DNA libraries. However, as the number of primer pairs increases drastically from a few pairs to several hundred or even several thousand pairs in a single reaction, primer dimer formation during multiplex PCR and the interference of the resultant primer dimers in the subsequent library preparation steps become an obstacle to successful NGS applications. Thus, there is a need for methods, compositions, and kits for preparing DNA sequencing libraries in a streamlined, high throughput, and low cost manner for both biomedical and agricultural applications.

BRIEF DESCRIPTION OF THE DRAWINGS

FIG. 1A presents a schematic of DNA library preparing using the processes disclosed herein. DNA targets of interest are PCR amplified with primers modified with phophorothioate linkages at the 3' end (black regions of the primers). PCR products are then digested with a combination of T7 exonuclease and Klenow Fragment and subsequently ligated with NGS adapters using T4 DNA ligase. Ligation products are purified and sequenced by a NGS platform.

FIG. 6 presents an image of an ethidium bromide-stained 10% polyacrylamide gel. Lane A: undigested 3,072-plex PCR product. Lane B; T7 exonuclease and Klenow polymerase digested 3,072-plex PCR product. Lane C: sequencing adapter primer amplified undigested library of 3,072-plex library. Lane D: sequencing adapter primer amplified digested library of 3,072-plex library. Lane E: DNA Ladder (Sigma-Aldrich). The DNA ladder from bottom to top: 50 bp, 100 bp, 200 bp, 300 bp, 400 bp, 500 bp, etc. Lane F: No Template sample as control for A. Lane G: No Template sample as control for B. Lane H: No Template sample as control for C. Lane I: No Template sample as control for D. Lanes C and H (undigested) have a doublet at approximately 150 bp, which is consistent with adapter-to-primer dimer ligation amplification products. Lanes D and I (digested) lack this doublet. These results demonstrate that digestion with T7 exonuclease and Klenow fragment improves the sequencing library quality by reducing the primer-dimer ligation products in the library.

SUMMARY

One aspect of the present disclosure encompasses a process for preparing a plurality of amplified nucleic acid products with reduced non-specific amplification artifacts. The first step of the process comprises contacting one or more nucleic acids with at least one pair of amplification primers under amplification conditions to form a plurality of amplification products, wherein each amplification primer comprises at least three nuclease-resistant groups in its 3' region. The process further comprises contacting the plurality of amplification products with a 5' to 3' exonuclease and either a 3' to 5' single strand-specific exonuclease or a proofreading polymerase to form a plurality of digested amplification products, wherein the plurality of digested amplification products has a reduced level of non-specific amplification artifacts as compared to a standard nucleic acid amplification reaction performed with primers devoid of nuclease-resistant groups. In some embodiments, the non-specific amplification artifacts are primer dimer products. In certain iterations, the non-specific amplification artifacts are reduced at least about 50%, at least about 75%, or at least about 90% as compared to the standard nucleic acid amplification reaction. In general, each of the plurality of digested amplification products has a phosphate group at its 5' end. Depending upon the enzymes used during the digestion step, each of the plurality of digested amplification products is blunt-ended or each of the plurality of digested amplification products has a 3' overhang.

In some embodiments, the nucleic acid(s) to be amplified is genomic DNA, organelle DNA, cDNA, or RNA. In certain embodiments, the nuclease-resistant groups are chosen from phosphorothioate bonds, 2' O-methyl groups, 2' fluoro groups, or a combination thereof. In specific embodiments, the nuclease-resistant groups are phosphorothioate bonds. In further embodiments, the 5' to 3' exonuclease is chosen from T7 exonuclease, T5 exonuclease, lambda exonuclease, RecJ$_f$, or combination thereof. In specific embodiments, the 5' to 3' exonuclease is T7 exonuclease. In certain embodiments, the 3' to 5' single strand-specific exonuclease is chosen from exonuclease I, exonuclease T, or combination thereof. In other embodiments, the proofreading polymerase is chosen from T4 DNA polymerase, Klenow DNA polymerase, Pfu DNA polymerase, Vent DNA polymerase, Pwo DNA polymerase, KOD DNA polymerase, T7 DNA polymerase, phi29 DNA polymerase, or combination thereof. In specific embodiments, the proofreading polymerase exonuclease is T4 DNA polymerase or Klenow DNA polymerase. In some embodiments, the process further comprises ligating one or more adaptors to the plurality of digested amplification products to form a plurality of adaptor-ligated amplification products.

Another aspect of the present disclosure provides a process for preparing a sequencing library. The process comprises contacting a plurality of nucleic acids with a plurality of amplification primer pairs under amplification conditions to form a plurality of amplification products, wherein each amplification primer comprises at least three nuclease-resistant groups in its 3' region. The next step of the process comprises contacting the plurality of amplification products with a 5' to 3' exonuclease and either a 3' to 5' single strand-specific exonuclease or a proofreading polymerase to form a plurality of digested amplification products. The final step of the process comprises ligating one or more adaptors to the plurality of digested amplification products to form the sequencing library.

A further aspect of the present disclosure encompasses a kit for preparing a plurality of amplification products devoid of non-specific amplification artifacts. The kit comprises (a) one or more pairs of amplification primers, wherein each amplification primer comprises at least three nuclease-resistant groups in its 3' region, (b) a 5' to 3' exonuclease, and (c) and either a 3' to 5' single strand-specific exonuclease or a proofreading polymerase.

Other aspects and iteration of the disclosure are described in more detail below.

DETAILED DESCRIPTION

Figure 1A:
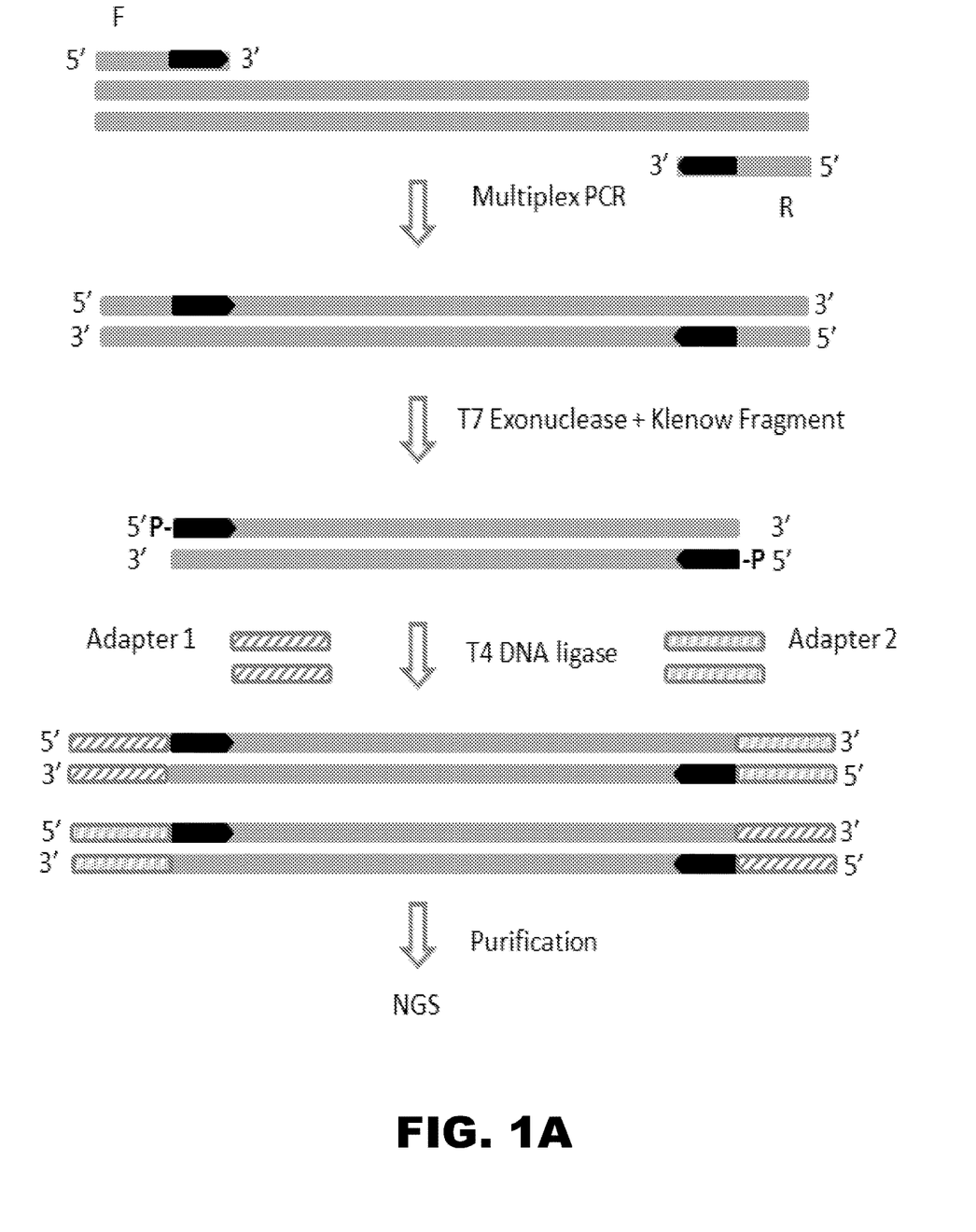
Figure 1B:
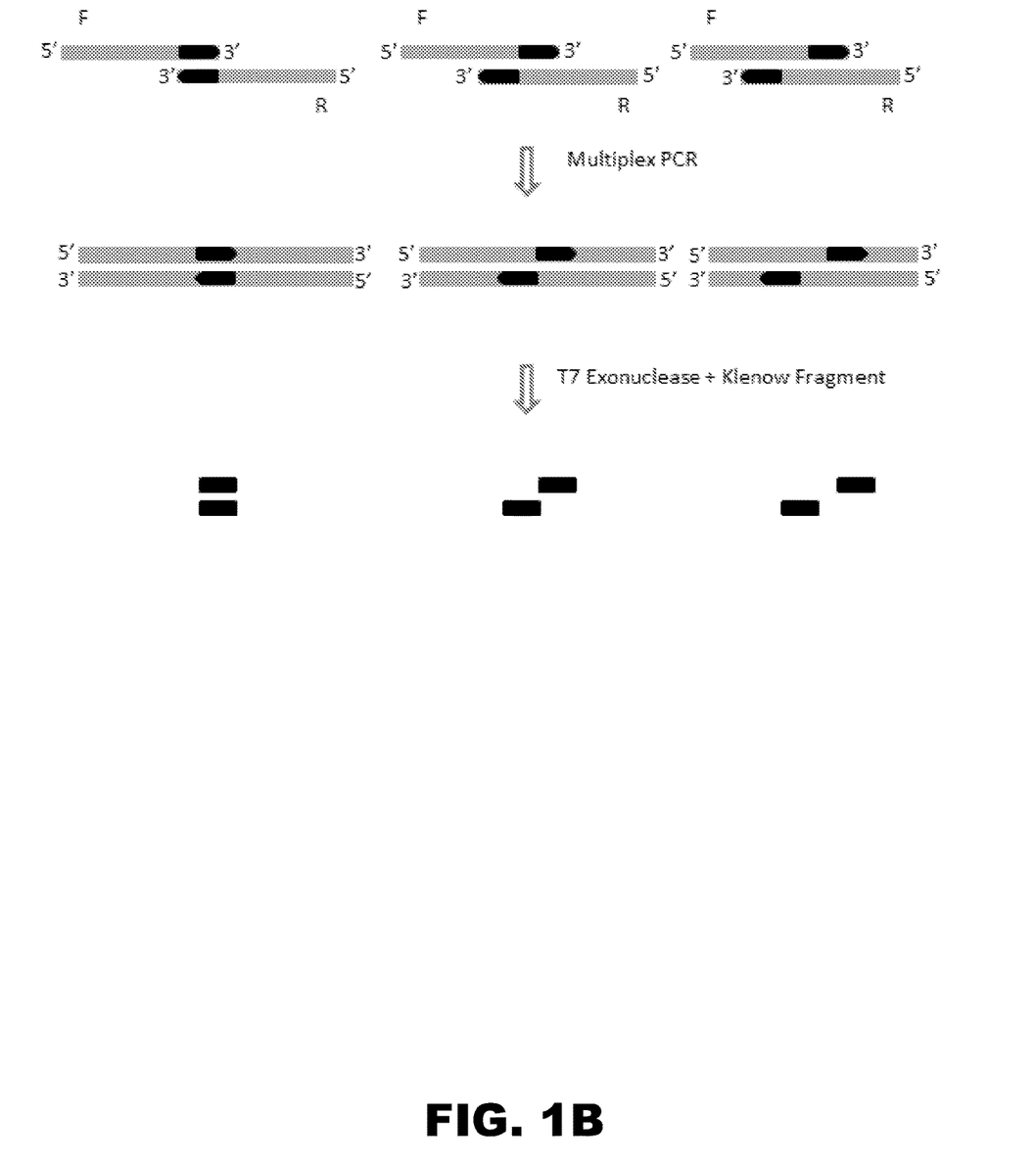
FIG. 1B diagrams the removal of primer dimers from the amplification reaction using the processes disclosed herein. Potential primer dimers produced during PCR are digested to small oligomers by T7 exonuclease and Klenow Fragment and thus excluded from competing with target DNA PCR fragments in ligation with NGS adapters.

The present disclosure provides processes and kits for preparing a plurality of amplified nucleic acid products with reduced non-specific amplification artifacts. The process comprises amplifying the desired target nucleic acids using amplification primers, each of which comprises at least three nuclease-resistant groups in the 3' region. The process further comprises digesting the resultant amplification products with a 5' to 3' exonuclease and either a 3' to 5' single strand-specific exonuclease or a proofreading polymerase such that nuclease sensitive nucleotides are removed from the ends of the amplification products, and primer dimers formed during the amplification reaction are degraded to short oligonucleotides comprising the nuclease-resistant groups (see FIG. 1A and FIG. 1B). The processes and kits disclosed herein, therefore, provide efficient, streamlined, high throughput, and low cost means for preparing libraries suitable for next generation sequencing platforms or other downstream applications.

I. Processes for Preparing a Plurality of Amplification Products

One aspect of the present disclosure provides processes for preparing a plurality of amplified nucleic acid products with reduced non-specific amplification artifacts. In general, the process comprises contacting one or more nucleic acids with at least one pair of amplification primers under amplification conditions to form a plurality of amplification products, wherein each amplification primer comprises at least three nuclease-resistant groups in its 3' region. The process further comprises contacting the plurality of amplification products with a 5' to 3' exonuclease and either a 3' to 5' single strand-specific exonuclease or a proofreading polymerase to form a plurality of digested amplification products, wherein the plurality of digested amplification products has a reduced level of non-specific amplification artifacts as compared to a standard nucleic acid amplification reaction performed with primers devoid of nuclease-resistant groups.

(a) Amplification Step

The first step of the process comprises contacting one or more nucleic acid(s) of interest with at least one pair of amplification primers under amplification condition to amplify the nucleic acid(s). Each amplification primer is an oligonucleotide comprising at least three nuclease-resistant groups in its 3' region.

(i) Amplification Primers Comprising Nuclease-Resistant Groups

Each amplification primer comprises at least three nuclease-resistant groups in its 3' region. A variety of nuclease-resistant groups can be included in the amplification primers disclosed herein. Suitable nuclease-resistant groups include phosphorothioate bonds, phosphorodithioate bonds, phosphoroamidite bonds, phosphorodiamidite bonds, amide bonds, 2' O-methyl groups, 2' fluoro groups, propyne bases, or combinations thereof. In some embodiments, the nuclease-resistant groups can be phosphorothioate bonds. In another embodiment, the nuclease-resistant groups can be a combination of phosphorothioate bonds and 2' O-methyl groups or 2' fluoro groups. Those of skilled in the art appreciate that other combinations are possible.

In some embodiments, each amplification primer comprises at least three, at least four, at least five, at least six, at least seven, at least eight, at least nine, at least ten, or more than ten nuclease-resistant groups in its 3' region. In specific embodiments, each amplification primer comprises four, five, six, seven, eight, nine, or ten nuclease-resistant groups in its 3' region. In certain embodiments, each amplification primer comprises five, six, seven, or eight phosphorothioate bonds in its 3' region. Each amplification primer can further comprise one, two, three, or four 2' O-methyl groups and/or 2' fluoro groups in its 3' region.

As used herein, the 3' region refers to a portion of the oligonucleotide primer closest to the 3' end of the molecule. In some embodiments, the nuclease resistant groups can be located within the ultimate, penultimate, and antepenultimate nucleotides at the 3' end of the molecule (i.e., the 3'-most 1-3 nucleotides), within the 3'-most 1-6 nucleotides, within the 3'-most 1-9 nucleotides, within the 3'-most 1-12 nucleotides, or within the 3'-most 1-15 nucleotides.

The length of the amplification primers can vary from about 10 nucleotides to about 40 nucleotides. In some embodiments, the amplification primers can range from about 10 to about 15 nucleotides in length, from about 15 to about 20 nucleotides in length, from about 20 to about 25 nucleotides in length, from about 25 to about 30 nucleotides in length, from about 30 to about 35 nucleotides in length, or from about 35 to about 40 nucleotides in length. In specific embodiments, the amplification primers can range from about 18 to about 27 nucleotides in length.

In general, the amplification primers are single-stranded, have complementarity to the nucleic acid(s) of interest, and each has a hydroxyl group at the 3' end for priming DNA synthesis. The amplification primers can comprise deoxyribonucleotides, ribonucleotides, or combinations thereof. The nucleotides can be standard nucleotides (i.e., A, C, G, T, and/or U) or nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include locked nucleic acids (LNA) and morpholinos. The amplification primers can also comprise a mix of nucleotides having 2-fold degeneracy (i.e., R, Y, K, M, S, and/or W), 3-fold degeneracy (i.e., B, D, H, and/or V), or 4-fold degeneracy (i.e., N).

The amplification primers can be designed using readily available primer design software (e.g., Primer3, PrimerQuest Tool, NPprimer, Multiplex primer design, etc.). In general, the amplification primers can have an average GC content of about 40-60%, and an average melting temperature (Tm) of about 58° C. to about 65° C. The amplification primers can be synthesized using standard oligonucleotide chemical synthesis methods, and the nuclease-resistant groups can be incorporated using well-known methods. The amplification primers can comprise one or more pair of primers, e.g., tens of pairs of primers, hundreds of pairs of primers, or thousands of pairs of primers.

The concentration of each amplification primer in the amplification reaction can range from about 1 nM to about 500 nM, depending, e.g., upon the number of primer pairs and the complexity of the target nucleic acid(s). In some embodiments, the concentration of each amplification primer can range from about 1-10 nM, from about 10-30 nM, from about 30-100 nM, from about 100-300 nM, or from about 300-500 nM. In certain embodiments, the concentration of each amplification primer can range from about 10 nM to about 200 nM. In other embodiments, the concentration of each amplification primer can range from about 5 nM to about 50 nM.

In specific embodiments, the one or more pairs of amplification primers can range in length from about 20 to 25 nucleotides, comprise standard deoxyribonucleotides, and contain from 5 to 8 phosphorothioate linkages at the 3' end of each primer.

(ii) Target Nucleic Acids

The one or more nucleic acids to be amplified by the process disclosed herein can and will vary. In some embodiments, the target nucleic acid(s) can be genomic DNA. The genomic DNA can be nuclear, mitochondrial, or plastid. In other embodiments, the target nucleic acid(s) can be complementary DNA (cDNA) transcribed from messenger RNA (mRNA) or non-coding RNA (e.g., micro RNA (miRNA), long noncoding RNA (lncRNA), long intergenic non-coding RNA (lincRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), and/or telomerase RNA component). In specific embodiments, the nucleic acids are genomic DNA or cDNA. Persons skilled in the art are familiar with means (e.g., standard protocols, commercially available kits, etc.) for isolating genomic DNA and preparing cDNA.

The target nucleic acids can be wild-type, can contain single nucleotide polymorphisms (SNPs), can contain multiple nucleotide substitutions, can contain insertions and/or deletions (indels), and/or can contain epigenetic modifications (e.g., methylated cytosines, other modified nucleotides, and the like).

The nucleic acid can be derived from eukaryotic, archaeal, or bacterial cells. Suitable eukaryotic cells include mammalian cells (e.g., human, primates, dogs, cats, farm animals, zoo animals, rodents, research animals, etc.), non-mammalian vertebrate cells (e.g., poultry, fish, frog, and the like), plant cells (e.g., maize, legumes, grasses, brassicas, and so forth), invertebrate cells (e.g., insects, worms, etc.), fungal cells, single-celled organisms, and the like.

(iii) Amplification Conditions

The first step of the process comprising contacting one or more nucleic acids with at least one pair of amplification primers under amplification conditions to form a plurality of amplification products. In general, the amplification conditions comprise contact with a DNA polymerase and deoxyribonucleotides (e.g., dNTPs) in the presence of a suitable buffer. In general, the DNA polymerase used for amplification has polymerase activity and 3' to 5' proofreading exonuclease activity, and can further comprise 5' to 3' exonuclease activity and/or terminal transferase activity. The DNA polymerase can be thermophilic (e.g., Taq DNA polymerase, Pfu DNA polymerase, Tli DNA polymerase, Tfl DNA polymerase, Tth DNA polymerase, Tli DNA polymerase, Bst DNA polymerase, Vent DNA polymerase, Deep Vent DNA polymerase, Pwo DNA polymerase, KOD DNA polymerase, variants thereof, or combinations thereof). Alternatively, the DNA polymerase can be mesophilic (e.g., E. coli DNA polymerase I, Klenow fragment of E. coli DNA polymerase I, phi29 DNA polymerase, T7 DNA polymerase, T4 DNA polymerase, variants thereof, or combinations thereof).

The amplification reaction can be a PCR-based amplification method (e.g., multiplex PCR, long range PCR, routine PCR, fast PCR, Hot Start PCR, touchdown PCR, and the like), multiple displacement amplification (MDA), transcription mediated amplification (TMA), nucleic acid sequence-based amplification (NASBA), strand displacement amplification (SDA), loop-mediated isothermal amplification (LAMP), helicase-dependent amplification (HAD), nicking enzyme amplification reaction (NEAR), rolling circle amplification (RCA), or ligation mediated amplification.

In one embodiment, the nucleic acids are amplified using a PCR-based process; e.g., multiplex PCR. The amplification conditions comprise contact with a thermophilic DNA polymerase, dNTPs, and a buffer suitable for PCR (which are known in the art). Each PCR cycle generally comprises 3 steps (i.e., denaturation, annealing, and extension); the total number of cycles can range from about 25 to about 50. The temperature of the denaturation step can range from about 90° C. to about 100° C., and the duration of the denaturation step can range from about 10 seconds to about 10 minutes. The temperature of the annealing step can varies depending upon the melting temperatures of the amplification primers. For example, the temperature of the annealing step can range from about 50° C. to about 65° C., and the duration of the annealing step can range from about 20 seconds to about 4 minutes. The temperature of the extension step can range from about 68° C. to about 75° C., and the duration of the extension step can vary from about 20 seconds to about 4 minutes. The final extension step can be followed by a terminal elongation step that lasts for about 5 minutes, 10 minutes, or longer.

(b) Digestion Step

The process further comprises contacting the plurality of amplification products formed in the first step with a 5' to 3' exonuclease and either a 3' to 5' single strand-specific exonuclease or a proofreading polymerase to form a plurality of digested amplification products. Contact of the amplification products with the 5' to 3' exonuclease removes nuclease sensitive nucleotides from the 5' ends of the amplification products until one or more nuclease-resistant nucleotides are encountered; each of the 5' ends has a phosphate group (see FIG. 1A). Contact with the 3' to 5' single strand-specific exonuclease removes the resultant 3' overhangs, or contact with the proofreading polymerase removes the resultant 3' overhangs and/or adds 3' adenine overhangs. The end result is that the plurality of digested amplification products will be blunt-ended or have 3' overhangs. When primer dimers or primer-dimer products that are generated during the amplification reaction, however, are contacted with the 5' to 3' exonuclease and the 3' to 5' single strand-specific exonuclease or the proofreading polymerase, short oligonucleotides are generated (see FIG. 1B). The resulting short oligonucleotides comprise the 3' regions of the amplification primers comprising the nuclease-resistant groups. The digestion step, therefore, generates digested amplification products ready for downstream reactions, but more importantly, reduces or eliminates primer-dimer products from subsequent reactions.

(i) 5' to 3' Exonuclease

Exonucleases are enzymes that hydrolyze phosphodiester bonds and remove nucleotides one at a time from either end of a nucleic acid chain. Exonucleases with 5' to 3' activity remove nucleotides from the 5' end. The 5' to 3' exonuclease can recognize and cleave single-stranded and/or double-stranded DNA templates. Non-limiting examples of suitable 5' to 3' exonucleases include T7 (gene 6) exonuclease, T5 exonuclease, lambda exonuclease, $RecJ_f$, or combinations thereof. In specific embodiments, the 5' to 3' exonuclease is T7 exonuclease.

In general, the amount of 5' to 3' exonuclease that is contacted with the amplification products can range from about 0.01 to about 20 units of enzyme. In some embodiments, the amount of 5' to 3' exonuclease can range from about 0.01 unit to about 1 unit, from about 1 unit to about 3 units, from about 3 units to about 10 units, or from about 10 units to about 20 units.

(ii) 3' to 5' Single Strand-Specific Exonuclease and Proofreading Polymerase

Single strand-specific exonuclease (ssExo) with 3' to 5' activity remove nucleotides from the 3' end of single-stranded nucleic acids. Examples of suitable 3' to 5' single strand-specific exonucleases include exonuclease I, exonuclease T, or combinations thereof. In some embodiments, the exonuclease I can be derived from *E. coli, Pyrococcus furiosus* (Pfu), or *Thermococcus thermophilus* (Tth).

Proofreading polymerases have 3' to 5' exonuclease activity, but lack 5' to 3' exonuclease activity. The proofreading polymerase can be a mesophilic DNA polymerase, a thermophilic DNA polymerase, or a combination thereof. Non-limiting examples of suitable mesophilic proofreading DNA polymerases include Klenow DNA polymerase (i.e., Klenow fragment of *E. coli* DNA polymerase), T4 DNA polymerase, T7 DNA polymerase, phi29 DNA polymerase, or combinations thereof. Non-limiting examples of suitable thermophilic proofreading DNA polymerases include Pfu DNA polymerase, Vent DNA polymerase, Deep Vent DNA polymerase, Pwo DNA polymerase, KOD DNA polymerase, Taq DNA polymerase, Tli DNA polymerase, Tfl DNA polymerase, Tth DNA polymerase, Tli DNA polymerase, Bst DNA polymerase, or combinations thereof.

The amount of the 3' to 5' single strand-specific exonuclease or the proofreading polymerase that is contacted with the amplification products can range from about 0.01 to about 20 units of enzyme. In some embodiments, the amount of DNA polymerase used in the reaction can range from about 0.01 units to about 1 unit, from about 1 unit to about 3 units, from about 3 units to about 10 units, or from about 10 units to about 20 units.

(iii) Reaction Conditions

The temperature of the reaction generally will vary depending upon the identity of the enzymes used in the digestion step. In some embodiments, the digestion can proceed at a single temperature. For example, the digestion can proceed at a temperature from about 10° C. to about 40° C., from about 20° C. to about 30° C., or about room temperature. In other embodiments, the digestion can proceed at two different temperatures, i.e., a first temperature followed by a second temperature. For example, the first temperature can range from about 10° C. to about 40° C., from about 20° C. to about 30° C., or about room temperature, and the second temperature step can range from about 40° C. to about 85° C., or from about 50° C. to about 75° C. The duration of the digestion step can range from about 5 minutes to about 180 minutes. In various embodiments, the reaction can proceed for a period of time from about 5 minutes to about 20 minutes, from about 20 minutes to about 40 minutes, from about 40 minutes to about 90 minutes, or from about 90 to about 180 minutes.

In some embodiments, the digestion enzymes can be inactivated by heat at the end of the reaction. For this, the reaction mixture can be heated to a temperature that ranges from about 60° C. to about 70° C., from about 70° C. to about 80° C., or from about 80° C. to about 90° C. for a period of time ranging from about 1 minutes to about 120 minutes depending upon the temperature of inactivation of the specific enzyme.

In general, the plurality of digested amplification products has a reduced level of non-specific amplification artifacts as compared to a standard nucleic acid amplification reaction performed with primers devoid of nuclease-resistant groups. In some embodiments, the level of non-specific amplification artifacts can be reduced at least about 50%, at least about 60%, at least about 70%, at least about 80%, at least about 90%, or at least about 95% as compared to the standard nucleic acid amplification reaction. In certain embodiments, the plurality of digested amplification products is essentially devoid of non-specific amplification artifacts.

The plurality of digested amplification products can be used directly in subsequent reactions or downstream applications without any intervening purification steps. Alternatively, the digested amplification products can be purified from nucleotides, amplification primers, enzymes, and salts using well-known nucleic acid purification methods (e.g., PCR purification kits, etc.).

(c) Optional Ligation Reaction

In some embodiments, the plurality of digested amplification products can be ligated with one or more adaptors to form a plurality of adaptor-ligated amplification products. The adaptors can be sequencing adaptors. In some embodiments, the adaptors can be suitable for NGS applications. For example, the adaptors can be linear adaptors (e.g., Illumina/Solexa adaptors, TruSeq adaptors, SOLiD adaptors, TA adaptors, NEBNext adaptors, 454 adaptors, barcoded adaptors, and the like), circular adaptors, or bubble adaptors. In some embodiments, adaptors generally can be blunt ended and non-phosphorylated. In other embodiments, the adaptors can contain 3' T overhangs and 5' phosphate groups.

The ligation is performed in the presence of a ligation enzyme (i.e., a ligase that catalyzes the formation of phosphodiester bonds). In general, the ligase is specific for double-strand DNA and catalyzes blunt end ligation or T/A ligation. Examples of suitable DNA ligases include, without limit, T4 DNA ligase, T3 DNA ligase, or combinations thereof. In specific embodiments, the DNA ligase is T4 DNA ligase. The amounts of ligase and adaptors to be included in the reaction, as well as reaction conditions, can and will vary, the determination of which is within the skill set of a person of ordinary skill in the art.

The processes described above also can be used to prepare a sequencing library. For this, the plurality of amplification products is generated by contacting a plurality of nucleic acids with a plurality of amplification primer pairs under amplification conditions, wherein each amplification primer comprising at least three nuclease-resistant groups as detailed above. The plurality of amplification products is then contacted with a 5' to 3' exonuclease and either a 3' to 5' single strand-specific exonuclease or a proofreading polymerase to form a plurality of digested amplification products. Lastly, adaptors are ligated to the digested amplification products as described above, thereby forming the sequencing library.

(d) Downstream Applications

In some embodiments, the plurality of adaptor-ligated amplification products can be sequenced using a next generation sequencing (NGS) platform. Non-limiting examples of NGS platforms include ion torrent sequencing, SOLiD sequencing, Illumina sequencing, genome analyzer sequencing, 454 sequencing, directional deep sequencing, nanoball sequencing, single molecule read time sequencing, and the like. NGS technologies include clinical diagnostics, cancer diagnostics, molecular diagnostic tests, cancer therapeutics, drug development, microbiome technologies, food and agricultural technologies, and basic research.

In other embodiments, the plurality of adaptor-ligated amplification products or plurality of digested amplification products can be used in other applications such as SNP genotyping, qPCR and PCR-based mutation detection methods, STR/microsatellite analysis, microarray-based technologies, RFLP and Southern blot analysis, and the like.

II. Kits

Another aspect of the present disclosure encompasses kits for preparing a plurality of amplification products with reduced non-specific amplification artifacts. In general, each kit comprises (a) one or more pairs of amplification primers, each amplification primer comprising at least three nuclease-resistant groups in its 3' region, (b) a 5' to 3' exonuclease, and (c) a 3' to 5' single strand-specific exonuclease or a proofreading polymerase. Suitable amplification primers are detailed above in section (I)(a)(i), suitable 5' to 3' exonucleases are described above in section (I)(b)(i), and suitable 3' to 5' single strand-specific exonucleases and proofreading polymerases are described above in section (I)(b)(ii).

The kits may further comprise one or more adaptors and/or a ligase, as detailed above in section (I)(c). The kits may further comprise one or more suitable buffers for each enzyme or combination thereof.

The kits provided herein generally include instructions for carrying out the processes detailed above. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

As various changes could be made in the above-described processes and kits without departing from the scope of the invention, it is intended that all matter contained in the above description and in the examples given below, shall be interpreted as illustrative and not in a limiting sense.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides. A or C or G or T). Nucleotides having 3-fold degeneracy include "B" (can be C or G or T), "D" (can be A or G or T), "H" (can be A or C or T), and "V" (can be A or C or G). Nucleotides having 2-fold degeneracy include "K" (can be G or T), "M" (can be A or C), "R" (can be A or G), "Y" (can be C or T), "S" (can be C or G), and "W" (can be A or T).

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

The following example illustrates certain aspects of the invention.

Figure 2:
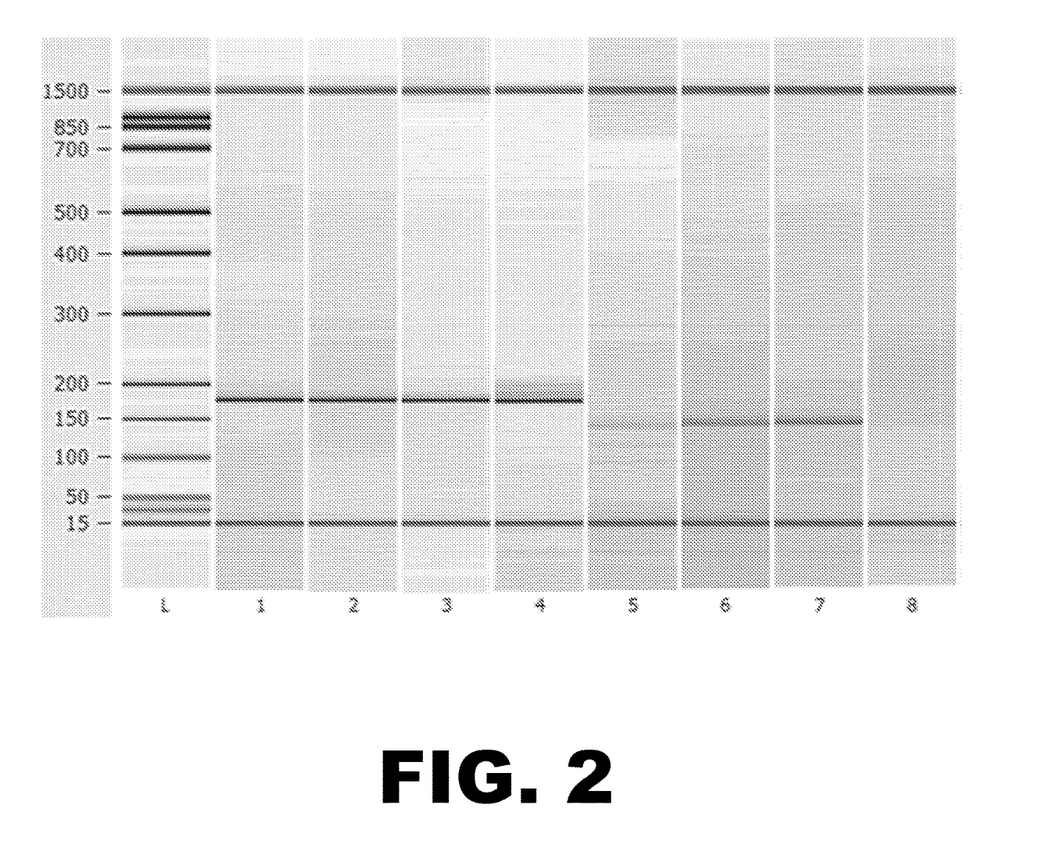
FIG. 2 illustrates that PCR fragments amplified from primers modified with 4-6 phosphorothioate linkages at the 3' end are protected from digestion by T7 exonuclease and Klenow fragment. Shown is a BioAnalyzer image of size fractionated digested PCR products and undigested controls. (L) BioAnalyzer DNA1000 Ladder. (1) Undigested product amplified from primers with 4 phosphorothioate linkages. (2) Undigested product amplified from primers with 5 phosphorothioate linkages. (3) Undigested product amplified from primers with 6 phosphorothioate linkages. (4) Undigested product amplified from unmodified control primers. (5) Digested product amplified from primers with 4 phosphorothioate linkages. (6) Digested product amplified from primers with 5 phosphorothioate linkages. (7) Digested product amplified from primers with 6 phosphorothioate linkages. (8) Digested product amplified from unmodified control primers. The results demonstrate that primer modification with phosphorothioate linkages at the 3' end can protect the resultant PCR fragments from degradation by T7 exonuclease and Klenow fragment.

Example 1: Amplification and Digestion of PCR Fragments Amplified with Modified Primers Maize genomic DNA was PCR amplified with modified or unmodified primers using JumpStart Taq ReadyMix (Sigma-Aldrich). The modified primers each contained 4-6 phosphorothioate linkages at the 3' end. The forward primer was 5'-CCACGGTGCCAAGTCCGTTTGA-3' (SEQ ID NO:1) and the reverse primer was 5'-AGGCGACGA-CATGGGTCAGTCA-3' (SEQ ID NO:2). Each reaction mixture contained 200 nM of each primer. PCR amplification was performed with 95° C./2 minutes of initial denaturation; 34 cycles of 94° C./30 seconds, 60° C./30 seconds, and 72° C./30 seconds; and 72° C./5 minutes. PCR products were then digested with 5 units each of T7 exonuclease and Klenow Fragment for 30 minutes at 22° C. Digested PCR products were size fractionated and quantified on a Bioanalyzer (Agilent). The results demonstrate that primer modification with phosphorothioate linkages at the 3' end protected the resultant PCR fragments from degradation by T7 exonuclease and Klenow Fragment (see FIG. 2).

Figure 3:
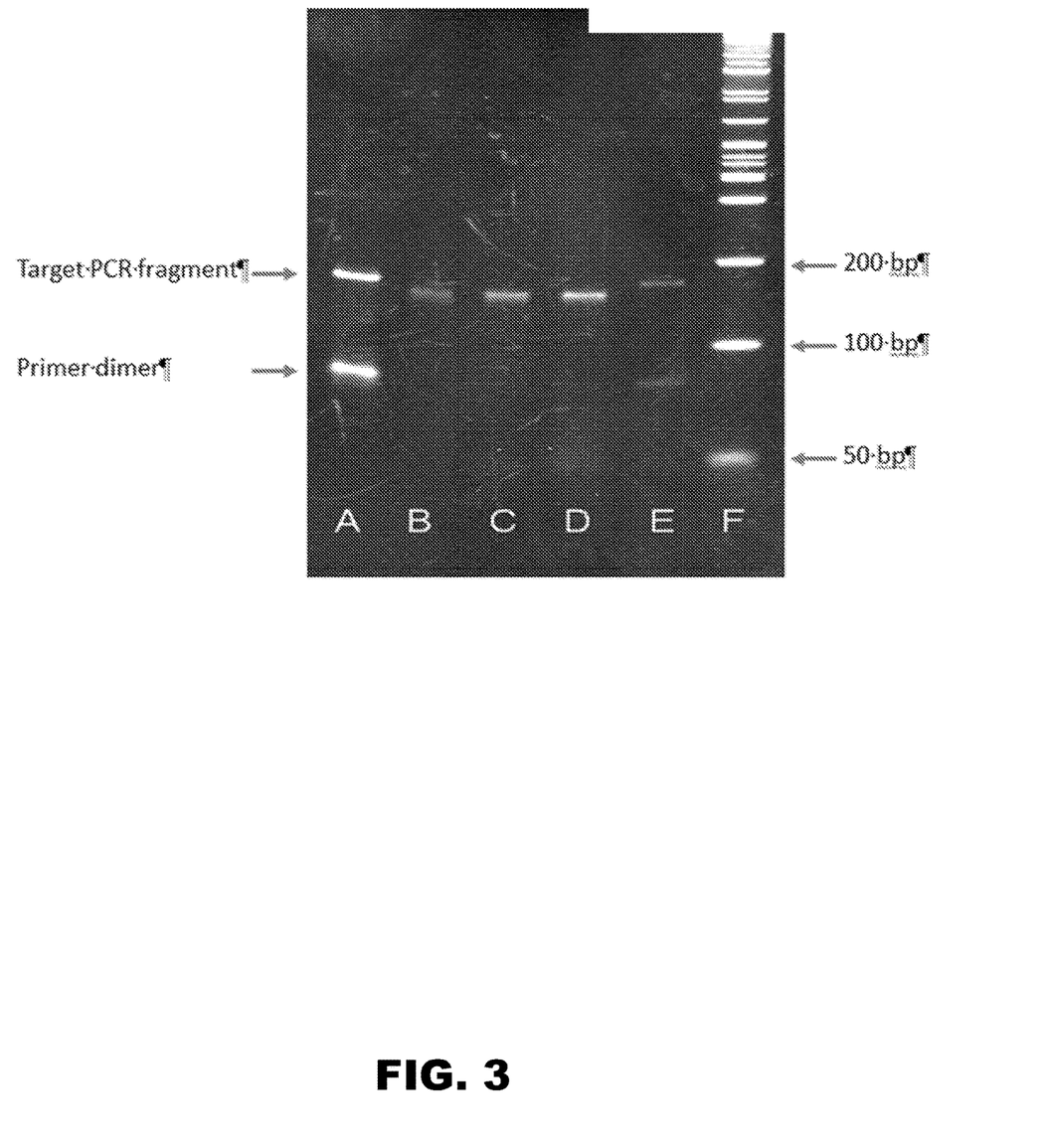
FIG. 3 shows removal of primer dimers by digestion with a combination of T7 exonuclease and Klenow fragment. Each primer was modified with 6 phosphorothioate linkages at the 3' end. An artificial primer dimer was generated with a pair of artificial primers, each of them also containing 6 phosphorothioate linkages at the 3' end. The PCR product and the primer dimer were combined and digested with different levels of T7 exonuclease and Klenow Fragment. Shown is an image of a 10% polyacrylamide gel of the size fractionated PCR fragment and primer dimer. (A) PCR product and primer dimer. (B) 5 units each of T7 exonuclease and Klenow. (C) 2.5 units each of T7 exonuclease and Klenow digestion. (D) 1 unit each of T7 Exonuclease and Klenow. (E) No enzyme digestion control. (F) DNA Ladder (Sigma-Aldrich). The results demonstrate that primer dimers can be selectively degraded from target DNA PCR fragments by a combination of T7 exonuclease and Klenow Fragment when PCR amplification is performed with primers modified with phosphorothioate linkages.

Example 2: Removal of Primer Dimers in PCR Fragments Amplified with Modified Primers Maize genomic DNA was PCR amplified with forward primer 5'-CCACGGTGCCAAGTCCGTTTGA-3' (SEQ ID NO:1) and reverse primer 5'-AGGCGACGA-CATGGGTCAGTCA-3' (SEQ ID NO:2), using JumpStart Taq ReadyMix. The primers were each modified with 6 phosphorothioate linkages at the 3' end. An artificial primer dimer was generated with a pair of artificial primers, each of them also containing 6 phosphorothioate linkages at the 3' end. Each reaction mixture contained 200 nM of each primer. PCR amplification was performed with 95° C./2 minutes of initial denaturation; 34 cycles of 94° C./30 seconds, 60° C./30 seconds, and 72° C./30 seconds; and 72° C./5 minutes. The PCR product and the primer dimer were combined and digested with 5 units each, 2.5 units each, or 1 unit each of T7 exonuclease and Klenow Fragment at 22° C. for 30 minutes, and resolved on a 10% polyacrylamides gel. The results demonstrate that primer dimers (but not target DNA PCR fragments) were selectively degraded by a combination of T7 exonuclease and Klenow Fragment when PCR amplification is performed with primers modified with phosphorothioate linkages (see FIG. 3)

Figure 4:
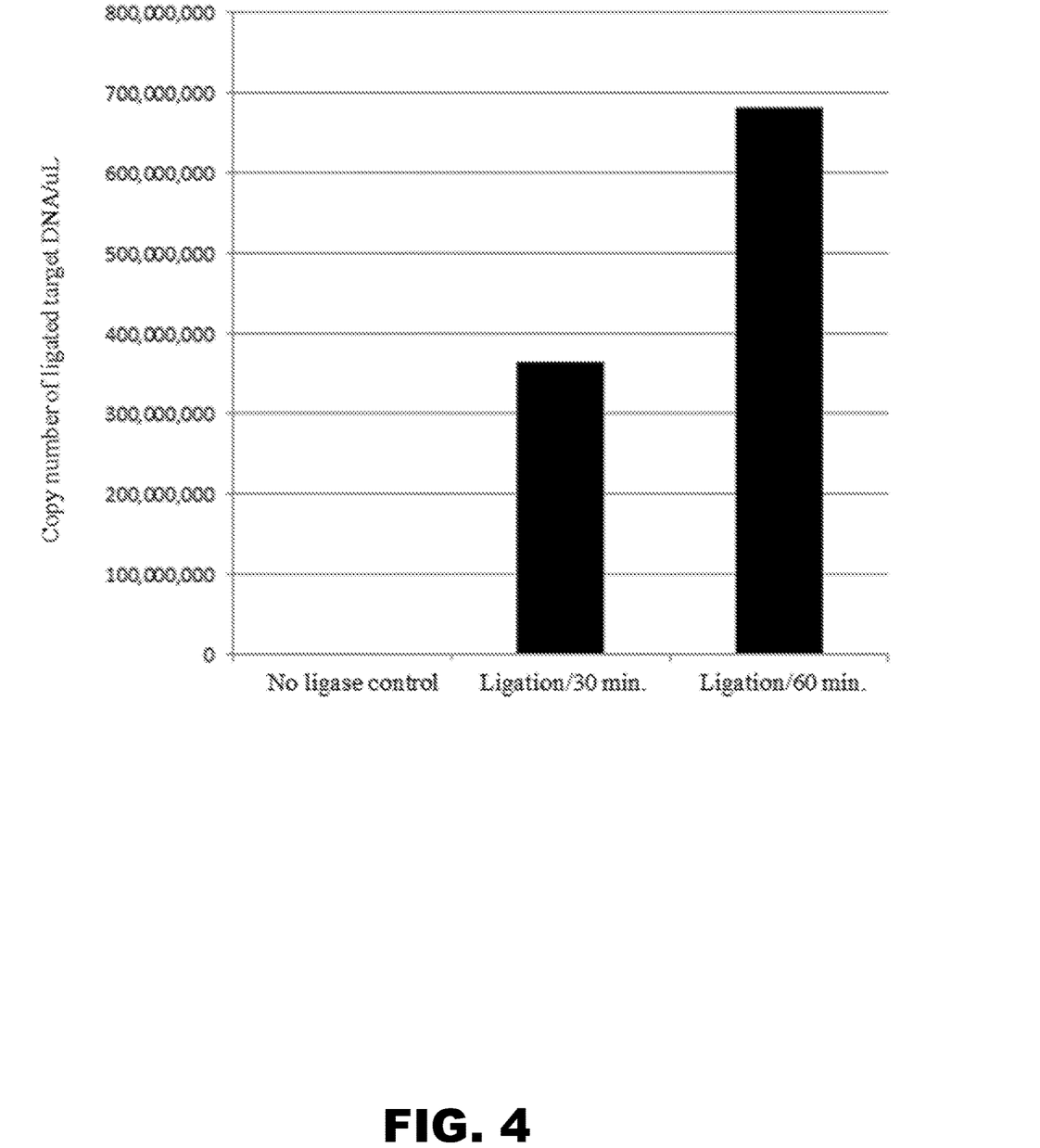
FIG. 4 illustrates ligation of maize target DNA PCR fragments with NGS adapters after digestion with T7 exonuclease and Klenow fragment. Maize DNA was amplified using modified primers as shown above in FIG. 2 and FIG. 3. Plotted is the copy number of ligated target DNA (quantified by TaqMan Real-Time PCR) for a sample without ligase and samples incubated with ligase for 30 or 60 minutes. The results demonstrate that PCR fragments amplified with primers containing phosphorothioate linkages at the 3' end can be digested with T7 exonuclease and Klenow Fragment and subsequently ligated with NGS adapters.

Example 3: Ligation of NGS Adaptors to Digested PCR Fragments Amplified with Modified Primers Maize genomic DNA was PCR amplified with forward primer 5'-CCACGGTGCCAAGTCCGTTTGA-3' (SEQ ID NO:1) and reverse primer 5'-AGGCGACGA-CATGGGTCAGTCA-3' (SEQ ID NO:2), using JumpStart Taq ReadyMix. The primers were each modified with 6 phosphorothioate linkages at the 3' end. Each reaction mixture contained 200 nM of each primer. PCR amplification was performed with 95° C./2 minutes of initial denaturation; 34 cycles of 94° C./30 seconds, 60° C./30 seconds, and 72° C./30 seconds; and 72° C./5 minutes. PCR products were then digested with 3 units each of T7 exonuclease and Klenow Fragment at 22° C. for 30 minutes, followed by 80° C. for 15 minutes to inactivate the enzymes. Digested PCR products were ligated with Ion Torrent P1 and A adapters at 22° C. for 30 or 60 minutes, followed by 72° C. for 10 minutes. Each reaction mixture contained 1 µM of adapters, 5% PEG 6000, and 80 units of T4 DNA ligase in 30 µL reaction. Ligation products were purified with a PCR purification kit and eluted in 30 µL of water. Ligated target DNA PCR fragments were quantified by TaqMan Real-Time PCR using a gene-specific TaqMan probe and primers specific to P1 and A adapters. The concentration of ligated target DNA PCR fragments was about 0.6 nM and 1.2 nM for the 30 minute and 60 minute ligation reactions, respectively. The results demonstrate that PCR products containing phosphorothioate linkages at the 3' ends can be digested with T7 exonuclease and Klenow Fragment and then subsequently ligated with NGS adapters (see FIG. 4).

Example 4: Ligation of NGS Adaptors to Human PCR Fragments

Figure 5:
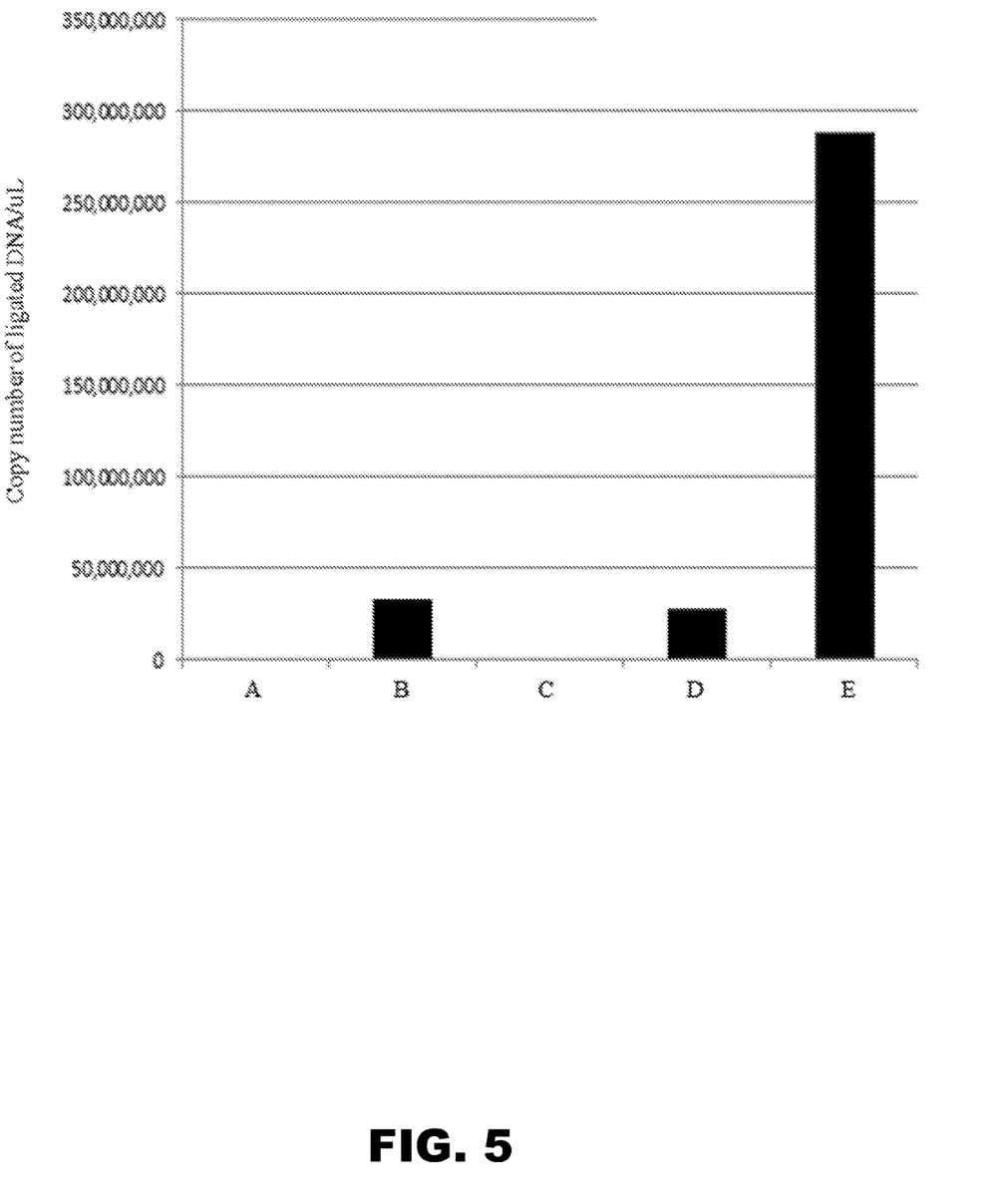
FIG. 5 shows ligation of human 384-plex PCR fragments with NGS adapters after digestion with T7 exonuclease and Klenow fragment. Human DNA was amplified with a pool of 384 pairs of primers modified at the 3' end with 5 phosphorothioate linkages, and the PCR products were digested with T7 exonuclease and Klenow fragment. Plotted is the copy number of ligated target DNA (quantified by TaqMan Real-Time PCR) for the following reactions. (A) No T4 DNA ligase control of adapters. (B) T4 DNA ligase control of adapters. (C) No T4 DNA ligase control of digested PCR products and adapters. (D) T4 DNA ligase control of undigested PCR products and adapters. (E) T4 DNA ligase ligation test of digested PCR products and adapters. The background ligation in the controls was caused by impurities in the T4 DNA ligase enzyme preparation, most likely a polynucleotide DNA kinase. The concentration of adapter ligated PCR fragments in test E was about 0.45 nM. The results demonstrate that highly multiplexed human DNA PCR fragments amplified with primers containing phosphorothioate linkages at the 3' end can be digested with T7 exonuclease and Klenow fragment and subsequently ligated with NGS adapters.

Human genomic DNA was PCR amplified with a pool of 384 pairs of primers using KAPA HiFi HotStart ReadyMix (KAPA Biosciences). The primers were a subset from a large primer set designed and published by a NIH human pancreatic cancer sequencing project. Each primer was modified with 5 phosphorothioate linkages at the 3' end of the primer. Each 384-plex PCR amplification reaction contained 10 nM of each primer. PCR amplification was performed with 95° C./2 minutes of initial denaturation; 30 cycles of 98° C./20 seconds, 59° C./2 minutes, and 72° C./30 seconds; and 72° C./5 minutes. PCR products were digested with 3 units of T7 exonuclease and 5 units of Klenow Fragment at 22° C. for 30 minutes, followed by heat inactivation at 75° C. for 20 minutes. Digested PCR products were ligated with Ion Torrent P1 and A adapters at 22° C. for 30 minutes, followed by 72° C. for 10 minutes. Each ligation reaction contained 1 µM of adapters, 6% PEG 6000, and 80 units of T4 DNA ligase in 30 µL reaction. Ligation products were purified with Agencourt AMPure XP system (Beckman Coulter, Inc.) and eluted in 30 µL of water. Purified products were quantified by TaqMan Real-Time PCR using a P1 adapter-specific TaqMan probe and primers specific to P1 and A adapters. As shown in FIG. 5, highly multiplexed human DNA PCR fragments amplified with primers containing phosphorothioate linkages at the 3' end can be digested with T7 exonuclease and Klenow Fragment and subsequently ligated with NGS adapters.

Example 5: Comparison of Adapter Ligated Libraries Comprised of Digested and Undigested 3,072-Plex PCR Products A set of 3,072 primer pairs were designed to amplify Zea mays genome regions ranging in length from 120 to 300 nucleotides. Each primer was modified with 6 phosphorothioate linkages at the 3' end. Zea mays genomic DNA was PCR amplified with this pool of 3,072 pairs of primers. PCR amplification of the target regions was performed in 10 µL containing 0.75 units of JumpStart™ AccuTaq™ LA Polymerase (Sigma-Aldrich), 300 µM each dNTP, 5 ng Zea mays genomic DNA, 5 mM $MgCl_2$, 1.5%/v DMSO, 50 mM Tris-HCl, 15 mM ammonium sulfate (pH 9.3), 0.1% Tween-20, and the 3,072-plex primer pool, with each primer at 7.5 nM. PCR amplification was performed with 96° C./2 minutes of initial denaturation; 34 cycles of 94° C./20 seconds, 59° C./2 minutes 30 seconds, and 68° C./30 seconds; and a final extension of 68° C./5 minutes. A no template control (i.e. no genomic DNA) reaction was run under identical conditions.

Following PCR, samples were either (i) digested with a combination of nucleases and dA-tailed or (ii) phosphorylated and dA-tailed. The nuclease digestion was conducted in a 12.5 µL reaction containing 10 µL of the PCR products, 1.5 units of T7 exonuclease (New England BioLabs Inc.), 1.5 units of DNA Polymerase I Large Klenow Fragment (New England BioLabs Inc.), 1.44 mM DTT, and 16 mM $MgCl_2$. The digestion reaction was incubated for 30 minutes at 25° C. Immediately after the digestion reaction, 0.5 µL of a mixture of 1.25 U/µL JumpStart™ Taq DNA Polymerase (Sigma-Aldrich) and 5 mM dATP was added and mixed. The reaction was then incubated for 20 minutes at 72° C. This step simultaneously adds 3' dA overhangs to amplicons and heat inactivates the T7 exonuclease and Klenow polymerase. For comparison, the undigested sample was phosphorylated and dA-tailed in a 13 µL reaction consisting of 10 µL of the PCR products, 0.625 units of JumpStart™ Taq DNA Polymerase (Sigma-Aldrich), 5 units of T4 polynucleotide kinase (New England BioLabs Inc.), 192 µM additional dATP, 5 mM DTT, 10 mM $MgCl_2$. The phosphorylation and dA-tailing reaction was incubated for 37° C. for 30 minutes, followed by 20 minutes at 72° C. to heat inactivate the enzymes.

The digested and undigested samples were each ligated with Illumina sequencing adapters in 50 µL reactions to produce sequencing libraries. Each ligation reaction contained 800 units of T4 DNA ligase (New England BioLabs Inc.), 700 nM Illumina compatible P5 and P7 adapter-duplex, 12%/v PEG 6000, 50 mM Tris pH 7.4, 10 mM $MgCl_2$, 10 mM DTT, and 1 mM ATP. The 50 µL ligation reactions were incubated for 30 minutes at 20° C. The sequencing libraries were analyzed by electrophoresis on a 10% polyacrylamide gel after PCR amplification in a 10 μL reaction using 1 μL of 1:100 dilution of each library, 5 μL of 2× JumpStart™ Taq ReadyMix™ (Sigma-Aldrich), and 200 nM P5 and P7 adapter specific PCR Primers. No template control samples were also run. The thermal cycling conditions were 95° C./2 minutes of initial denaturation; 18 cycles of 95° C./15 seconds, 59° C./20 seconds, and 72° C./20 seconds, with a final extension of 72° C./5 minutes.

Figure 6:
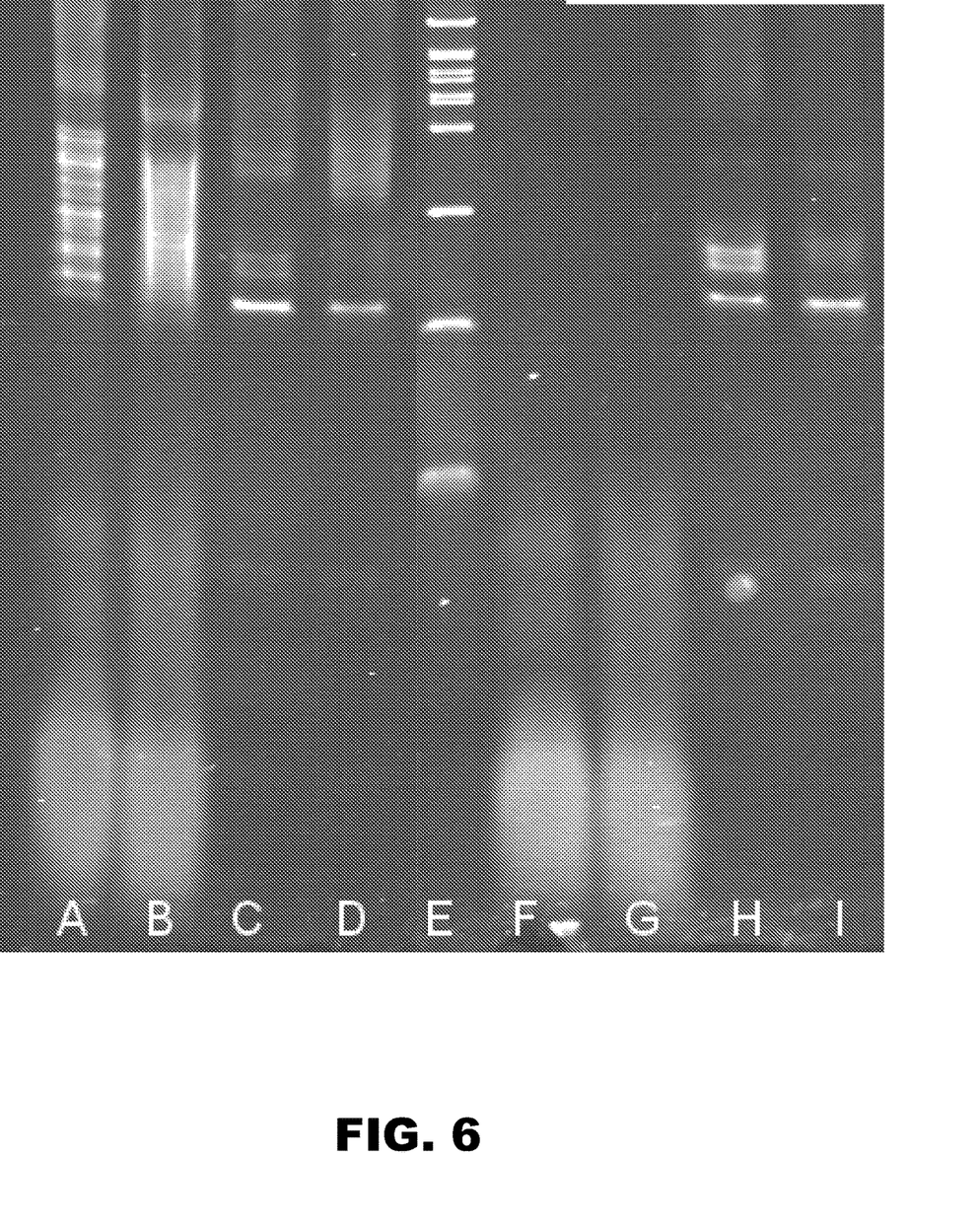

The results are shown in FIG. 6. Lanes C and D contained sequencing adapter primer-amplified undigested library and digested library samples, respectively. Lanes H and I contained the no template control samples for the sequencing adapter primer-amplified undigested library and digested library samples, respectively. In each of these lanes there is a band just above the 100 bp marker band that is consistent with sequencing adapter-to-adapter ligation amplification product. Above this band at approximately 150 bp in undigested lanes C and H are bands consistent with adapter-to-primer dimer ligation amplification products. These bands are not present in digested lanes D and I. These results demonstrate that digestion of the 3,072-plex PCR products with T7 exonuclease and Klenow fragment improves the sequencing library quality by reducing the primer-dimer ligation products in the library.

What is claimed is:

1. A process for preparing a plurality of amplified nucleic acid products with reduced non-specific amplification artifacts, the process comprising:
   a) contacting one or more nucleic acids with at least one pair of amplification primers under amplification conditions to form a plurality of amplification products, each amplification primer comprising at least five nuclease-resistant groups in its 3' region and wherein the nuclease resistant groups are phosphorothioate bonds;
   b) contacting the plurality of amplification products with a 5' to 3' exonuclease and either a 3' to 5' single strand-specific exonuclease or a proofreading polymerase to form a plurality of digested amplification products, wherein the plurality of digested amplification products has a reduced level of non-specific amplification artifacts as compared to a standard nucleic acid amplification reaction performed with primers devoid of nuclease-resistant groups.

2. The process of claim 1, wherein each of the plurality of digested amplification products has a phosphate group at its 5' end.

3. The process of claim 1, wherein each of the plurality of digested amplification products is blunt-ended or each of the plurality of digested amplification products has a 3' overhang.

4. The process of claim 1, wherein the 5' to 3' exonuclease is chosen from T7 exonuclease, T5 exonuclease, lambda exonuclease, RecJ$_f$, or a combination thereof.

5. The process of claim 1, wherein the 3' to 5' single strand-specific exonuclease is chosen from exonuclease I, exonuclease T, or a combination thereof.

6. The process of claim 1, wherein the proofreading polymerase is chosen from T4 DNA polymerase, Klenow DNA polymerase, Pfu DNA polymerase, Vent DNA polymerase, Pwo DNA polymerase, KOD DNA polymerase, T7 DNA polymerase, phi29 DNA polymerase, or a combination thereof.

7. The process of claim 1, wherein the non-specific amplification artifacts are primer dimer products.

8. The process of claim 1, wherein the non-specific amplification artifacts are reduced at least about 50%, at least about 75%, or at least about 90% as compared to the standard nucleic acid amplification reaction.

9. The process of claim 1, further comprising ligating one or more adaptors to the plurality of digested amplification products to form a plurality of adaptor-ligated amplification products.

10. The process of claim 9, wherein the ligating proceeds without purification of the plurality of digested amplification products, or the ligating proceeds after purification of the plurality of digested amplification products.

11. The process of claim 1, wherein the one or more nucleic acids used in step (a) is genomic DNA or complementary DNA (cDNA).

12. A kit for preparing a plurality of amplification products devoid of non-specific amplification artifacts, the kit comprising:
- a) one or more pairs of amplification primers, each amplification primer comprising at least five nuclease-resistant groups in its 3' region and wherein the nuclease resistant groups are phosphorothioate bonds;
- b) a 5' to 3' exonuclease; and
- c) either a 3' to 5' single strand-specific exonuclease or a proofreading polymerase.

13. The kit of claim 12, wherein the 5' to 3' exonuclease is chosen from T7 exonuclease, T5 exonuclease, lambda exonuclease, RecJ$_f$, or a combination thereof.

14. The kit of claim 12, wherein the 3' to 5' single strand-specific exonuclease is chosen from exonuclease I, exonuclease T, or a combination thereof.

15. The kit of claim 12, wherein the proofreading polymerase is chosen from T4 DNA polymerase, Klenow DNA polymerase, Pfu DNA polymerase, Vent DNA polymerase, Pwo DNA polymerase, KOD DNA polymerase, T7 DNA polymerase, phi29 DNA polymerase, or a combination thereof.

16. The kit of claim 12, further comprising one or more adaptors and a DNA ligase.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 1
ccacggtgcc aagtccgttt ga                                              22

<210> SEQ ID NO 2
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 2
aggcgacgac atgggtcagt ca                                              22